US 6,529,778 B2

(12) United States Patent  
Prutchi

(10) Patent No.: US 6,529,778 B2
(45) Date of Patent: Mar. 4, 2003

(54) FLUID-PHASE ELECTRODE LEAD

(75) Inventor: David Prutchi, Lake Jackson, TX (US)

(73) Assignee: Impulse Dynamics N.V., Curacao (AN)

( * ) Notice: Subject to any disclaimer, the term of this patent is extended or adjusted under 35 U.S.C. 154(b) by 145 days.

(21) Appl. No.: 09/736,974

(22) Filed: Dec. 14, 2000

(65) Prior Publication Data

US 2001/0025193 A1 Sep. 27, 2001

(30) Foreign Application Priority Data

Dec. 19, 1999 (IL) .................................................. 133592

(51) Int. Cl.$^7$ ................................................. A61N 1/05
(52) U.S. Cl. ........................ 607/119; 607/98; 607/126; 607/116; 606/41
(58) Field of Search ........................... 607/119–123, 88, 607/89, 96, 98, 101, 102; 606/22, 41–50, 170, 171, 180

(56) References Cited

U.S. PATENT DOCUMENTS

| 5,458,630 A | | 10/1995 | Hoegnelid et al. | |
|---|---|---|---|---|
| 5,584,872 A | | 12/1996 | LaFontaine et al. | |
| 5,707,402 A | * | 1/1998 | Heim | 607/88 |
| 5,968,005 A | * | 10/1999 | Tu | 604/20 |
| 6,283,962 B1 | * | 9/2001 | Tu et al. | 606/41 |

* cited by examiner

Primary Examiner—Mark Paschall
(74) Attorney, Agent, or Firm—Reed Smith LLP

(57) ABSTRACT

A fluid-phase electrode lead apparatus is disclosed, for the delivery of electrical signals to an excitable tissue. The electrode lead comprises a catheter, having distal and proximal ends, at least one electrode provided at the distal end of said catheter, electrically connectable to an electric signal generator, and electrolytic fluid is provided through the catheter at the distal end to facilitate electric conduction of an electric signal from the at least one electrode to the excitable tissue.

7 Claims, 4 Drawing Sheets

FLUID-PHASE ELECTRODE LEAD

FIELD OF THE INVENTION

The present invention relates to electrode leads. More particularly it relates to an electrode lead for the delivery of electrical signals to a muscle tissue with metallic electrode and an electrolytic fluid serving as a fluid-phase interface between the electrode and muscle tissue.

BACKGROUND OF THE INVENTION

Conventional metallic electrodes had been described in the art as means for delivering electrical pulses for the control of skeletal or cardiac muscles, See for example PCT/IL97/00012 (published as WO 97/25098), titled ELECTRICAL MUSCLE CONTROL (Ben-Haim et al.) incorporated herein by reference, which disclosed a method and apparatus for locally controlling the electrical and/or mechanical activity of cardiac muscle cells, in situ.

Cardiac pacing, defibrillation, as well as other electrical muscle control (hereafter referred to as—excitable tissue control, ETC) devices use electrodes to deliver electrical pulses that may vary in duration from 0.1 to 2 Ms (milliseconds) in the case of pacing up to 10 to 40 ms in the case of ETC.

In some other ETC applications, for example electronic cardioplegia, as described in US patent application Ser. No 09/320,091 (Ben-Haim et al.), filed Jun. 26, 1999 titled INDUCTION OF CARDIOPLEGIA USING APPLIED ELECTRICAL SIGNALS, electrical pulses may have a duration similar to that of the cardiac cycle (about 1s)

Operated under certain muscle-control protocols—especially those requiring relatively strong or long electrical pulses—an electrode may inflict local tissue damage caused by electrolytic and thermal mechanisms due to direct electrode-tissue interface (contact). This limits the range of waveforms and amplitudes that can be applied using metallic-phase electrodes or non-flowing ionic-phase electrodes (such as Ag—AgCl electrodes with gelled AgCl interface).

In the present invention the metallic electrode is not placed in direct physical contact with the muscle tissue. Instead coupling is achieved through the use of a flowing electrolytic fluid which promptly dissipates heat, prevents the formation of high-current density areas, and considerably reduces the contamination of the muscle tissue by electrolytes and sparing the tissue from direct electrolyte damage.

Although to the best knowledge of the applicants fluid-phase electrodes have never been described as the delivery means for stimulating or muscle-control signals, electrodes with flowing electrolytic medium had been described as means for delivering radio-frequency (RF) energy for the purpose of creating lesions in the cardiac tissue. See for example U.S. Pat. No. 5,676,693 (LaFontaine), titled ELECTROPHYSIOLOGY DEVICE, incorporated herein by reference.

The use of flowing electrolyte had also been described as a means for reducing the conductivity of tissue in vicinity to an ablation electrode in U.S. Pat. No. 5,431,649 (Muller et al.), titled METHOD AND APARATUS FOR RF ABLATION, incorporated herein by reference.

In general however, the delivery of fluids to the vicinity of an electrode had not been used to form a fluid-phase electrical interface between a metallic-phase electrode and the target muscle tissue. Rather, fluid delivery to the vicinity of an electrode had been used to reduce localized tissue heating during ablation (see, for example, U.S. Pat. No 5,334,193 (Nardella), titled FLUID COOLED ABLATION CATHETER, U.S. Pat. No. 5,437,662 (Nardella), titled FLUID COOLED ELECTROSURGICAL CAUTHERIZATION SYSTEM, U.S. Pat. No. 5,520,684 (Imran), titled TRANSURETHRAL RADIO FREQUENCY APPARATUS FOR ABLATION OF THE PROSTATE GLAND AND METHOD). It had also been described as the mechanism for ablation (e.g. cryogenic ablation see U.S. Pat. 4,943,290 (Rexroth) titled ELECTROLYTE PURGING ELECTRODE TIP), as well as to pharmacological enhancement of the therapeutic effect of ablation (e.g. delivery of sclerotic agents as described in U.S. Pat. No. 5,403,311 (Abele et al.) titled ELECTRO-COAGULATION AND ABLATION AND OTHER ELECTROTHERAPEUTIC TREATMENTS OF BODY TISSUE), or delivery of chemotherapeutic agent to an ablated tumor site as described in U.S. Pat. No. 5,507,743 (Edwards) titled COILED RF ELECTRODE TREATMENT APPARATUS), all incorporated herein by reference.

It is an object of the present invention to provide an electrode for cardiac electrical tissue control whereby the metallic part of the electrode is not placed in direct physical contact with the cardiac tissue.

It is further an object of the present invention to provide such an electrode that uses electrolytic fluid as the coupling agent in order to prevent the creation of high-current density areas (hot spots), dissipate heat generated by Tissue Control signal on the target tissue, and considerably reduce the contamination of the target tissue by electrolytes and thus prevent direct electrolyte damage to the tissue.

Yet another object of the present invention is to provide such an electrode that allows the employment of a broader range of muscle-control waveforms and amplitudes than those which can be safely applied to the target tissue when using metallic-phase or non-flowing ionic-phase electrodes.

BRIEF DESCRIPTION OF THE INVENTION

It is thus perovided, in accordance with a preferred embodiment of the present invention, a fluid-phase electrode lead apparatus for the delivery of electrical signals to an excitable tissue comprising:

a catheter, having distal and proximal ends;

at least one electrode provided at the distal end of said catheter, electrically connectable to an electric signal generator;

means for providing electrolytic fluid to facilitate electric conduction of an electric signal from said at least one electrode to said excitable tissue.

Furthermore, in accordance with a preferred embodiment of the present invention, said at least one electrode is kept at a distance from said excitable tissue.

Furthermore, in accordance with a preferred embodiment of the present invention, said distance is in the range of 1 to 3 millimeters.

Furthermore, in accordance with a preferred embodiment of the present invention, said catheter is provided with an internal conduit through which said electrolytic fluid is provided.

Furthermore, in accordance with a preferred embodiment of the present invention, said apparatus is further provided with an internal conduit fluidically connected to means for providing vacuum to facilitate anchoring of said distal end of the catheter to said excitable tissue.

Furthermore, in accordance with a preferred embodiment of the present invention, said apparatus is further provided with an internal conduit fluidically connected to means for providing vacuum to facilitate anchoring of said distal end of the catheter to said excitable tissue.

Furthermore, in accordance with a preferred embodiment of the present invention, said internal conduit fluidically connected to means for providing vacuum further protrudes relatively to said internal conduit through which said electrolytic fluid is provided, both conduits provided with widening rims, and wherein said electrode is positioned near the rim of said internal conduit through which said electrolytic fluid is provided.

Furthermore, in accordance with a preferred embodiment of the present invention, said conduits are coaxial.

Furthermore, in accordance with a preferred embodiment of the present invention, said rims are flexible.

Furthermore, in accordance with a preferred embodiment of the present invention, the apparatus is further provided with a cap fluidically connected to said internal conduit through which said electrolytic fluid is provided.

Furthermore, in accordance with a preferred embodiment of the present invention, said electrode is provided on the inside of said cap.

Furthermore, in accordance with a preferred embodiment of the present invention, said cap is further provided with hooks serving as anchoring means for anchoring the cap to said excitable tissue.

Furthermore, in accordance with a preferred embodiment of the present invention, the apparatus is further provided with a cap, said cap provided with anchoring means for anchoring said cap to said excitable tissue, said cap also provided with an inlet and an outlet, said inlet fluidically connected to said internal conduit through which said electrolytic fluid is provided and said outlet fluidically connected to said internal conduit fluidically connected to means for providing vacuum.

Furthermore, in accordance with a preferred embodiment of the present invention, said anchoring means comprise two hooks.

Furthermore, in accordance with a preferred embodiment of the present invention, said electrode is made from a biocompatible material.

Furthermore, in accordance with a preferred embodiment of the present invention, said material is carbon-fiber or iridium-oxide-coated-titanium.

Furthermore, in accordance with a preferred embodiment of the present invention, said conduits walls are made of biocompatible material.

Furthermore, in accordance with a preferred embodiment of the present invention, said material is silicon or urethane.

Furthermore, in accordance with a preferred embodiment of the present invention, electrolytic fluid is sterile isotonic saline or Ringer's solution.

Finally, in accordance with a preferred embodiment of the present invention, said means for providing electrolytic fluid feeds the electrolytic fluid continuously.

BRIEF DESCRIPTION OF THE FIGURES

In order to better understand the present invention, and appreciate some practical applications, the following Figures are provided and referenced hereafter. It should be noted that the Figures are given as examples only and in no way limit the scope of the invention as defined in the appending Claims. Like components are denoted by like reference numerals.

DETAILED DESCRIPTION OF THE INVENTION AND FIGURES

As mentioned herein known metallic electrodes used to deliver electrical pulses to skeletal or cardiac muscles may cause localized tissue damage through electrolytic or thermal mechanisms due to direct electrode-tissue contact.

The present invention provides an electrode lead whose electrode (or electrodes) is not placed in direct physical contact with the target tissue. Rather coupling is achieved by the employment of an electrolytic fluid capable of efficiently dissipating heat, preventing the formation of high-current density areas (hot spots), considerably reducing the contamination of the muscle tissue by electrolytes and preventing direct electrolyte damage to the muscle tissue.

The use of the electrode lead of the present invention brings about the ability to apply a broader range of muscle-control waveforms and amplitudes, for example allowing the application of electrical pulses of sufficient duration and amplitude required for electronic cardioplegia.

Several preferred embodiments of the fluid-phase electrode lead, in accordance with a preferred embodiment of the present invention are presented herein, with reference to the Figures. These embodiments are merely presented for explanatory purpose and in no way limit the scope of the present invention as claimed in the appended Claims.

Figures 1A, 1B:
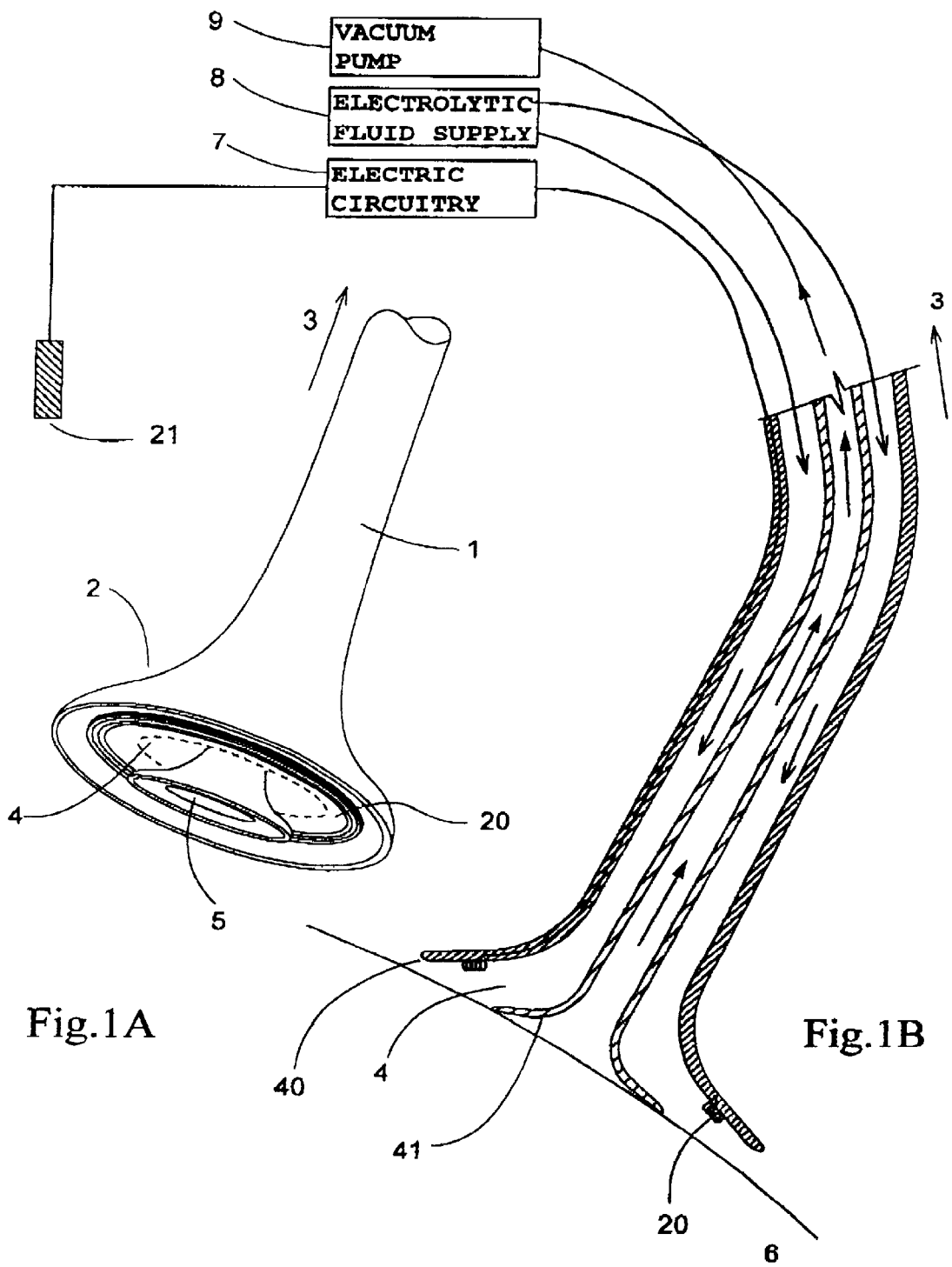
FIG. 1 illustrates a fluid phase electrode lead, in accordance with a preferred embodiment of the present invention, with vacuum anchoring means.

Reference is now made to FIG. 1, illustrating a fluid phase electrode lead, in accordance with a preferred embodiment of the present invention, with vacuum anchoring means FIG. 1A depicts an isometric view of the distal end of such lead and FIG. 1B depicts a sectional view of the lead.

The electrode lead comprises an elongated body 1 having a distal end 2 and a proximal end 3, having two coaxial conduits 4, 5, passing through it.

Each of the coaxial conduits has a dilated rim 40, 41, at the distal end 2 of the lead, with an electrode 20 positioned on the surface of the external conduit rim 40 from the inside and with the internal conduit rim 41 protruding from the external conduit rim so that when the internal conduit rim is in contact with a surface (e.g. the epicardium 6), the electrode 20 situated on the external conduit rim 40 is kept at a distance from that surface having no physical contact with the surface.

The electrode is electrically connected to an electric circuitry 7 of a signal generating device, such as the electric tissue controller disclosed in detail in PCT application PCT/IL97/00012 (International Publication Number WO 97/25098) to Ben-Haim et al., titled "ELECTRICAL MUSCLE CONTROLLER", incorporated herein by reference, or other electrical pulse generator. A second electrode 21, which may be an electrode of the type disclosed in the present invention or of a different type, is provided for the purpose of completing the circuit.

The internal conduit 5 is fluidically connected to a vacuum pump 9, so that when the pump is activated and the distal end of the electrode lead brought near the muscle surface (the epicardium 6, as shown in FIG. 1) the dilated rim 41 of the internal conduit 5 is attached to the surface and held in position by the suction force.

The external conduit 4 is fluidically connected to an electrolytic fluid supply 8, which provides an electrolytic fluid through the conduit to the location of the electrode. When the volume between the electrode and the muscle surface is filled with electrolytic fluid it enables the electrical pulse generated by the electrical circuitry 7 and conducted to the electrode to be delivered to the muscle tissue.

The electrode 20 may be easily removed by simply pausing the vacuum pump operation, and gently pulling the electrode lead 1 away from the muscle tissue.

Figures 2A, 2B:
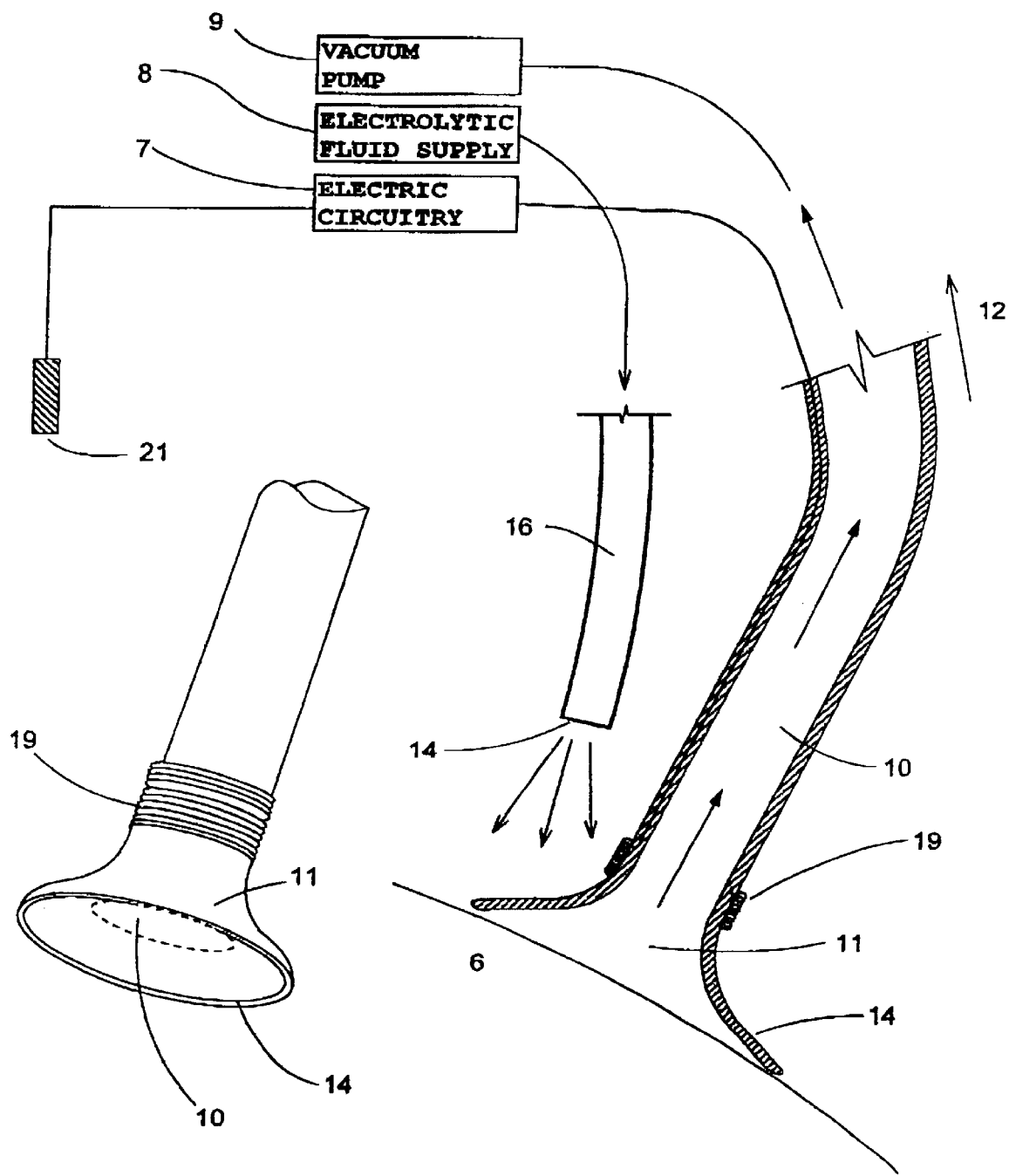
FIG. 2 illustrates a fluid phase electrode lead, in accordance with another preferred embodiment of the present invention, with vacuum anchoring means and a separate electrolytic fluid conduit.

FIG. 2 illustrates a fluid phase electrode lead, in accordance with another preferred embodiment of the present invention, again, with vacuum anchoring means. FIG. 2A is an isometric view of the lead and FIG. 2B is a sectional view of the lead.

The electrode lead comprises a conduit 10 having a distal end 11 and proximal end 12. The distal end of the conduit is provided with dilated rim 14. An electrode 19 is provided at the distal end 12, but not at the edge, so that some distance is kept between the electrode 19 and the muscle tissue 6 when the distal end 12 is in contact with the tissue 6. The electrode 19, here in the form of a coil, is electrically connected to an electric circuitry 7 providing the desired electrical pulse to be administered to the muscle tissue. The conduit is fluidically connected to a vacuum pump 9 providing suction so that when activated the distal end of the electrode lead is held in position on the target tissue 6.

An additional conduit 16 is provided connected to an electrolytic fluid supply 17, and its distal end 14 positioned in the vicinity of the distal end 11 of the electrode lead so that electrolytic fluid provided by electrolytic fluid supply 8 may flow over the distal end of the electrode lead and fill the gap between the electrode 19 and the target tissue 6, submerging or at least wetting the electrode.

Figure 3:
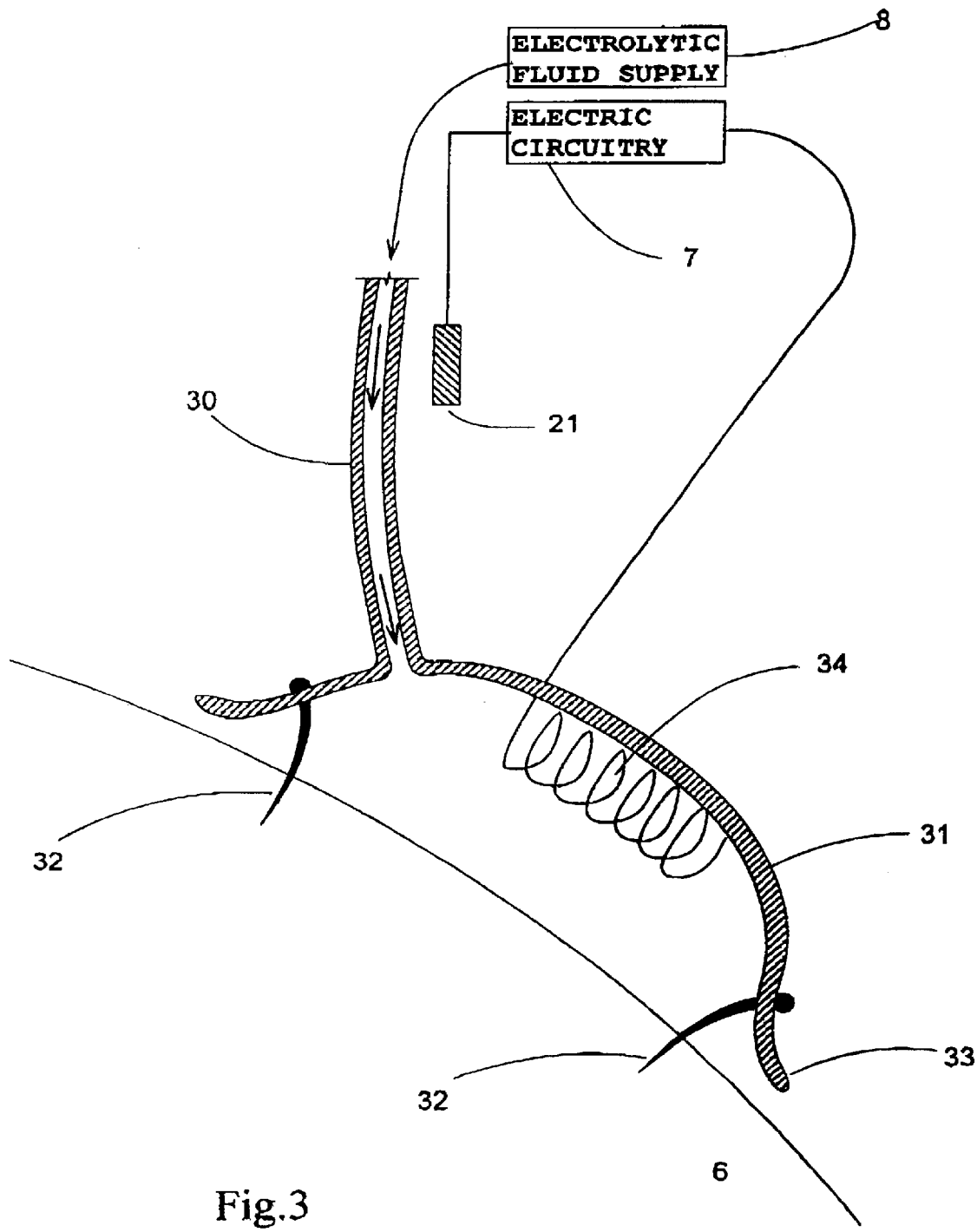
FIG. 3 illustrates a fluid phase electrode lead, in accordance with another preferred embodiment of the present invention, with hooks as anchoring means.

FIG. 3 illustrates a sectional view of a fluid phase electrode lead, in accordance with another preferred embodiment of the present invention, with hooks as anchoring means.

The electrode lead 30 comprises a conduit and is fluidically connected to a cap 31 provided at its distal end. The cap is provided with two hooks 32 which are used to engage the cap onto the muscle surface 6, and preferably has a widening rim to allow better coverage of the muscle surface. On the other hand it may be desirable to provide a cap without wider rim at its distal end when the muscle surface is rough or irregular, so that the will not be a need for a large quantity of electrolytic fluid to facilitate conduction of an electric signal to the muscle. An electrode 34 is provided inside cap 31, positioned on the internal wall of the cap but kept at a distance from its edges (away from the rim). The electrode is electrically connected to an electrical circuitry of a signal providing device having at least one additional electrode 21 for the completion of the circuit. Electrolytic fluid supply 8 fluidically connected to the lead provides electrolytic fluid which floods the inside of the cap to provide conductive medium for the electric signal generated by the signal generating device, from the electrode to the muscle surface.

Note that the cap does not sealingly cover the muscle surface. The electrolytic fluid is allowed to escape through opening at the rim 33 of the cap 31, thus dissipating heat from the electrode, and its presence in the vicinity of the muscle and the electrode 34 allows the delivery of electric signal from the electrode to the muscle through the electrolytic medium.

Figure 4:
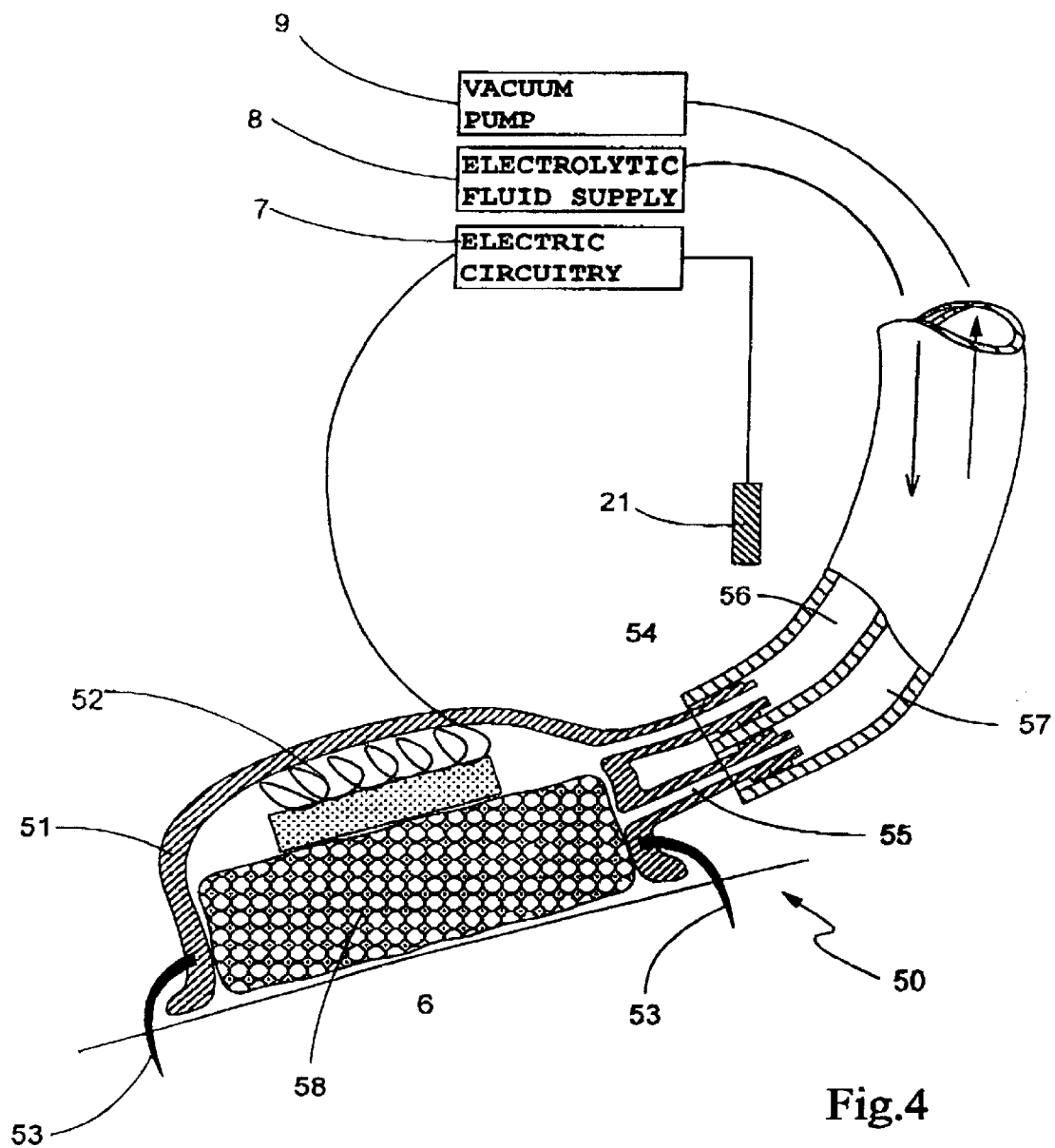
FIG. 4 illustrates a fluid phase electrode lead, in accordance with another preferred embodiment of the present invention, with a closed flow system and vacuum evacuation duct.

FIG. 4 illustrates sectional view of a fluid phase electrode lead, in accordance with another preferred embodiment of the present invention, with a closed flow system and vacuum evacuation duct.

The electrode lead 50 comprises a cap 51 provided with an electrode 52 on the inside of said cap, electrically connected to electric circuitry of a signal generating device 7. The cap is anchored to a muscle surface 6 by means of two hooks 53. Cap 51 is further provided with an inlet 54 and an outlet 55. The cap's inlet is fluidically connected to an electrolytic fluid supply 8, whereas the outlet 55 is fluidically connected to a vacuum pump 9. The connection to these devices comprises tubes 56, 57, or optionally coaxial twin duct as described in the Embodiment shown in FIG. 1. When vacuum pump 9 is activated the sub-pressure created inside the cap draws electrolytic fluid from the electrolytic fluid supply 8 into the cap. The fluid floods the cap and enables the electric signal generated by the signal generating device 7 to traverse through the fluid to the muscle. The flow of electrolytic fluid through the cap, past the electrode, allow heat generated on the electrode to dissipate. The vacuum pump 9 and electrolytic fluid supply may be connected in series thus allowing the electrolytic fluid to circulate through the cap.

The cap 51 may be also provided with a sponge or any other porous layer 58 which is designed to be soaked with the electrolytic fluid as it flows through the cap, thus enhancing the efficiency of the device. The embodiment described in this figure comprises a closed-flow system, as opposed to the embodiments shown in FIGS. 1–3.

The electrode (or electrodes) suitable for use in the electrode lead of the present invention should be a sufficiently biocompatible metallic electrode, preferably made to yield a very high interface capacitance (e.g. manufactured from materials such as carbon-fiber, iridium-oxide-coated titanium, etc.). As mentioned earlier it is positioned at the distal end of the electrode lead in such way that it cannot come in direct contact with the muscle tissue, or else it is likely to inflict the tissue the kind of damage the present invention seeks to prevent. The electrodes are electrically connected to the electric circuitry by electrical connecting means (wiring) insulated and preferably passing through the conduit wall. The conduit wall is preferably made of a biocompatible material, such as silicon or urethane, and it is recommended that the conduit wall, and in particular its distal end at the rim be rendered flexible so that it is does not present too hard an object to the muscle tissue, but not too soft so that it does not collapse inwardly when vacuum prevails within the conduit.

The electrolytic fluid used in the apparatus of the present invention may be sterile isotonic saline, Ringer's solution or any other biocompatible electrolytic fluid suitable for such task. The flowing electrolytic fluid dissipates the heat developed on the electrode and its surroundings, prevents the formation of high-current density areas, and considerably reduces the contamination of the muscle tissue by electrolytes, thus sparing the tissue from direct electrolyte damage.

The electrolytic fluid may be continuously fed to the device of the present invention, but it can also be operated in a predetermined timing corresponding to the application of the electrical signal by the electrode. It seems reasonable to irrigate the device continuously with the electrolytic fluid, as the gaps between consecutive signals may not suffice to allow the fluid to absorb heat and dissipate it.

The distance between the electrode and the muscle tissue surface, in the embodiments shown in the figures and in any other embodiment of the present invention should preferably be between 1 to 3 millimeters.

It is further noted that although the embodiments shown in the Figures constitute electrode leads having a single electrode, a multi-electrode lead embodiment of the present invention would be still covered by the scope of the present invention, as any person skilled in the art would find it elementary to replace a single electrode lead with a multi-electrode lead and implement the main aspect of the present invention on the multi-electrode lead.

It should be clear that the description of the embodiments and attached Figures set forth in this specification serves only for a better understanding of the invention, without limiting its scope as covered by the following Claims.

It should also be clear that a person in the art, after reading the present specification could make adjustments or amendments to the attached Figures and above described embodiments that would still be covered by the following Claims.

What is claimed is:

1. A fluid-phase electrode lead apparatus for the delivery of electrical signals to an excitable tissue comprising:
    a catheter, having distal and proximal ends;
    at least one electrode provided at the distal end of said catheter, electrically connectable to an electric signal generator;
    means for providing electrolytic fluid to facilitate electric conduction of an electric signal from said at least one electrode to said excitable tissue; and
    an internal conduit fluidically connected to means for providing vacuum to facilitate anchoring of said distal end of the catheter to said excitable tissue.

2. The apparatus as claimed in claim 1, wherein said apparatus is further provided with an internal conduit fluidically connected to means for providing vacuum to facilitate anchoring of said distal end of the catheter to said excitable tissue.

3. The apparatus as claimed in claim 2, wherein said internal conduit fluidically connected to means for providing vacuum further protrudes relative to said internal conduit through which said electrolytic fluid is provided, both conduits provided with widening rims, and wherein said electrode is positioned near the rim of said internal conduit through which said electrolytic fluid is provided.

4. The apparatus as claimed in claim 3, wherein said conduits are coaxial.

5. The apparatus as claimed in claim 3, wherein said rims are flexible.

6. The apparatus as claimed in claim 2, wherein it is further provided with a cap, said cap provided with anchoring means for anchoring said cap to said excitable tissue, said cap also provided with an inlet and an outlet, said inlet fluidically connected to said internal conduit through which said electrolytic fluid is provided and said outlet fluidically connected to said internal conduit fluidically connected to means for providing vacuum.

7. The apparatus as claimed in claim 6, wherein said anchoring means comprise two hooks.

* * * * *